United States Patent
Canós et al.

(10) Patent No.: US 9,815,758 B2
(45) Date of Patent: Nov. 14, 2017

(54) PROCESS OF PREPARING 4-METHYL-3-DECEN-5-ONE

(71) Applicant: International Flavors & Fragrances Inc., New York, NY (US)

(72) Inventors: Avelino Corma Canós, Valencia (ES); Sara Iborra Chornet, Valencia (ES); Alexandra Velty, Valencia (ES); Manuel Querol Sans, Castellón (ES); Amadeo Fernández Miranda, Benicarlo (ES); Jaime Renovell Gomez, Castellón (ES)

(73) Assignee: INTERNATIONAL FLAVORS & FRAGRANCES INC., New York, NY (US)

( * ) Notice: Subject to any disclaimer, the term of this patent is extended or adjusted under 35 U.S.C. 154(b) by 0 days.

(21) Appl. No.: 15/375,252

(22) Filed: Dec. 12, 2016

(65) Prior Publication Data

US 2017/0166504 A1    Jun. 15, 2017

(30) Foreign Application Priority Data

Dec. 14, 2015  (ES) .................................. 201531801

(51) Int. Cl.

| | |
|---|---|
| *C07C 45/59* | (2006.01) |
| *B01J 21/00* | (2006.01) |
| *B01J 23/00* | (2006.01) |
| *C07C 45/29* | (2006.01) |
| *B01J 23/52* | (2006.01) |
| *B01J 23/10* | (2006.01) |
| *B01J 23/66* | (2006.01) |
| *B01J 27/18* | (2006.01) |
| *B01J 23/68* | (2006.01) |
| *B01J 23/89* | (2006.01) |
| *B01J 21/18* | (2006.01) |
| *B01J 35/00* | (2006.01) |
| *B01J 37/04* | (2006.01) |
| *B01J 37/00* | (2006.01) |
| *B01J 37/02* | (2006.01) |

(52) U.S. Cl.
CPC ............... *C07C 45/29* (2013.01); *B01J 21/18* (2013.01); *B01J 23/10* (2013.01); *B01J 23/52* (2013.01); *B01J 23/66* (2013.01); *B01J 23/688* (2013.01); *B01J 23/8906* (2013.01); *B01J 27/1806* (2013.01); *B01J 35/0006* (2013.01); *B01J 35/0013* (2013.01); *B01J 37/0072* (2013.01); *B01J 37/0221* (2013.01); *B01J 37/0236* (2013.01); *B01J 37/04* (2013.01)

(58) Field of Classification Search
CPC .. C07C 45/59; B01J 21/00; B01J 23/00; B01J 37/00
USPC ......................................................... 568/408
See application file for complete search history.

(56) References Cited

FOREIGN PATENT DOCUMENTS

EP             1690848 A1        8/2006

OTHER PUBLICATIONS

Liu et al. Iron-Catalyzed Aerobic Oxidation of Allylic Alcohols: The issue of C=C Bond Isomerization. Organic Letters, 2013, vol. 15, No. 20, 5150-5153.*
Extended European Search Report for European Application No. 16203777.4 dated Apr. 20, 2017.
Alberto Abad et al : 11 A Coll aborati ve 1-13, Effect between Gol d and a Support Induces the Sel ecti ve Oxi dati on of Al cohol s11 , Ang Ewandte Chemi E Internati Onal Edition, vol. 44, No. 26, Jun. 27, 2005 (Jun. 27, 2005), pp. 4066-4069, XP055363273, ISSN: 1433-7851, DOI: 10.1002/ani e.200500382.
Villa A et al : 11 Ni trogen functi onal i zed 1-13 carbon nanostructures supported Pd and Au—Pd NPs as catal yst or al cohol s oxi dati on 11, Catalysis Today, Elsevi er, Amsterdam, N L, vol. 157, No. 1-4, Nov. 17, 2010 (Nov. 17, 2010) , pp. 89-93, XP027443979, ISSN: 0920-5861, DOI: 10.1016/J.ATTOD.2010. 01.052[retri eved on Feb. 21, 2010].

* cited by examiner

*Primary Examiner* — Sikarl Witherspoon
(74) *Attorney, Agent, or Firm* — Martin Zhang; XuFan Tseng; Elizabeth M. Stover

(57) ABSTRACT

A method of preparing 4-methyl-3-decen-5-one. The method includes the step of oxidizing 4-methyl-3-decen-5-ol in the presence of (i) oxygen and (ii) a metal catalyst, wherein the metal catalyst contains a catalytic metal deposited on nanoparticle support.

20 Claims, 1 Drawing Sheet

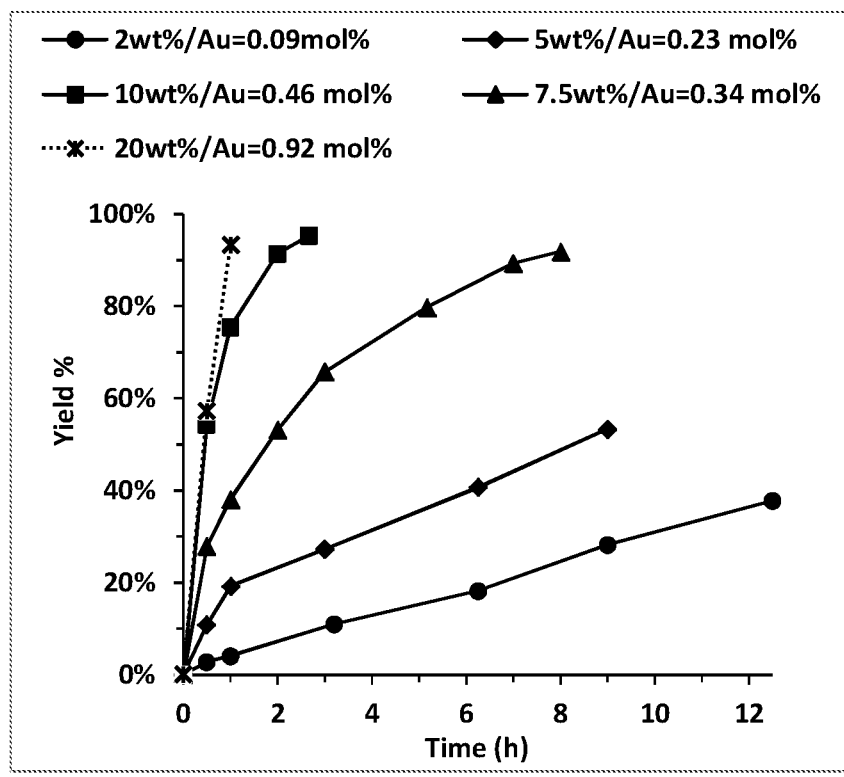

PROCESS OF PREPARING 4-METHYL-3-DECEN-5-ONE

FIELD OF THE INVENTION

The present invention relates to the preparation of 4-methyl-3-decen-5-one (Formula I) by oxidizing 4-methyl-3-decen-5-ol (Formula II) in the presence of a metal catalyst. 4-Methyl-3-decen-5-one is a fragrance ingredient useful in perfumes, toilet waters, colognes, personal products and the like.

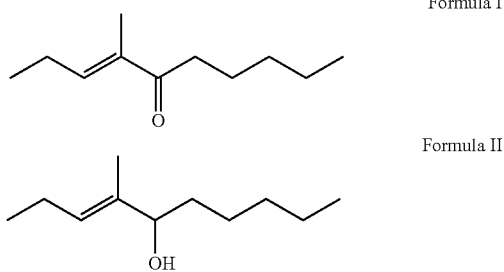

BACKGROUND OF THE INVENTION

The preparation of 4-methyl-3-decen-5-one was described in US Patent Application Publication No. 2006/0178291 A1 via the Oppenauer oxidation reaction using 45 mol % of aluminum isopropoxide and 3 equivalents of acetone based on the starting material 4-methyl-3-decen-5-ol. This reaction generates a large amount of solid waste due to the use of aluminum isopropoxide during industrial manufacturing. The solid aluminum waste is an environmental hazard and requires costly disposal.

Villa et al. reported oxidation of allylic alcohols such as cinnamyl alcohol using Au—Pd catalyst supported on carbon nanotubes. See Villa, et al., *Catalysis Today* 157, 89 (2010). Abad et al. studied the oxidation of secondary allylic alcohols to their corresponding ketones using gold nanoparticles deposited on nanocrystalline cerium oxide. See Abad et al., *Angewandte Chemie International Edition* 44, 4066 (2005) and *Chemical Communications* 2006, 3179. Other catalysts for oxidizing allylic alcohols include manganese dioxide, Osmium tetraoxide, Pt/Bi/graphite, and chromic acid. See Gritter et al., *J. Org. Chem.* 24 (8), 1051-56 (1959); Cha et al., *Tetrahedron* 40(12), 2247-55 (1984); Lee et al., *Green Chemistry* 2, 279-82 (2000); Harding et al., *J. Org. Chem.* 40, 1664-65 (1975). None of these oxidation reactions have been applied to prepare 4-methyl-3-decen-5-one.

There is a need to develop an efficient and environment friendly process to prepare 4-methyl-3-decen-5-one at large scale.

SUMMARY OF THE INVENTION

This invention is based on the discovery that 4-methyl-3-decen-5-one can be prepared at a high yield in a green process, namely, selectively oxidizing 4-methyl-3-decen-5-ol using a metal catalyst.

Accordingly, one aspect of this invention relates to a method of preparing 4-methyl-3-decen-5-one by oxidizing 4-methyl-3-decen-5-ol in the presence of (i) oxygen and (ii) a metal catalyst, wherein the metal catalyst contains a catalytic metal deposited on a nanoparticle support.

The catalytic metal is typically a hydrogenation metal. Non-limiting examples of the catalytic metal are Pd, Au, Pt, Ru, Rh, or any combination thereof. Au is a preferred catalytic metal. By weight of the metal catalyst, the catalytic metal (e.g., Au) is present in an amount of 0.1 to 10%.

The nanoparticle support is typically an organic or inorganic carrier selected from oxides of alkaline-earth metals, lanthanides, and p-bloc elements. Exemplary nanoparticle supports include iron oxide, titanium oxide, cerium oxide, zirconium oxide, alumina, charcoal, hydroxyapatite, or any combination thereof. These supports are in the form of nanoparticles having a particle size of 0.05 to 200 nanometers (e.g., 0.05 to 100 nm, 0.1 to 50 nm, and 0.1 to 25 nm).

In some embodiments, the metal catalyst further contains one or more doping metals such as alkali metals (e.g., Li, Na, K, Rb, and Cs), alkaline earth metals (e.g., Be, Mg, Ca, Sr, and Ba), and any combination thereof. The doping metal can also be Fe, Mn, or a combination thereof. These doping metals (e.g., Na, Fe, and Mn) are typically present in an amount of 0 to 50,000 ppm (e.g., 10 to 40,000 ppm, 10 to 10,000 ppm, 20 to 5,000 ppm, 50 to 3,000 ppm, and 100 to 2,000 ppm) by weight of the metal catalyst.

In any of the above described methods, oxygen can be provided in the form of an oxygen gas, air, stripped air, enriched air, or any combination thereof. The oxidization reaction is preferably carried out at a temperature of 20 to 240° C. (e.g., 40 to 140° C.) and at a pressure of 0.1 to 20 bars (e.g., 1 to 15 bars).

The any method described above, the oxidization reaction can be performed in the presence or absence of a solvent. Examples of the solvent include water, halogenated or non-halogenated alkyl and/or aromatic solvents, carboxylic acid solvents, and any combination thereof.

In some embodiments, the oxidization reaction is performed in a batch reactor. The metal catalyst is present in an amount of at least 1% (e.g., at least 3%, at least 6%, at least 6.5%, at least 7%, 1 to 50%, 6 to 50%, 3 to 40%, 6.5 to 40%, 5 to 20%, and 7 to 20%) by weight of 4-methyl-3-decen-5-ol. The catalytic metal (e.g., Au) is present in an amount of at least 0.05 molar % (e.g., at least 0.3 molar %, 0.01 to 10 molar %, 0.3 to 5 molar %, and 0.3 to 2 molar %) that of 4-methyl-3-decen-5-ol.

In other embodiments, the oxidization reaction is performed in a semicontinuous or continuous reactor. The continuous reactor can be a single Continuous Stirred Tank Reactor (CSTR), multiple CSTRs in series, or a microreactor.

A CSTR is an open system having a tank of a constant volume, a feed pipe, and an exit pipe. Both the feed pipe and exit pipe are separately connected to the tank. The starting material (4-methyl-3-decen-5-ol) is continuously introduced into the tank via the feed pipe and the product (4-methyl-3-decen-5-one) is continuously removed from the tank via the exit pipe. The reaction occurs within the tank. For exemplary chemical processes using CSTRs, see US Patent Application Publication No. 20150133694.

A microreactor is a device containing one or more reaction channels each having an internal diameter (ID) of 0.1 to 200 mm (e.g., 0.2 to 150 mm, 0.2 to 100 mm, 0.3 to 100 mm, 0.3 to 50 nm, and 0.4 to 50 mm, and 0.5 to 20 mm).

Both a CSTR and microreactor can be a packed bed reactor, wherein the reactor is packed with materials such as metal catalyst, glass beads (having a particle size of 10 to 100 μm). As used herein, the terms "packed" and "packing" mean to fill a reactor with one or more materials that allow efficient production of 4-methyl-3-decen-5-one. In one embodiment, the CSTR or microreactor is packed with a metal catalyst to 20 to 90% volume of the reactor.

The details of one or more embodiments of the invention are set forth in the description below. Other features, objects, and advantages of the invention will be apparent from the description, drawings, and claims.

BRIEF DESCRIPTION OF THE DRAWING

FIG. 1 shows the yield of 4-methyl-3-decen-5-one vs reaction time in five reactions each using a different amount of $Au/CeO_2$ catalyst.

DETAILED DESCRIPTION

4-Methyl-3-decen-5-one can be prepared at a high yield through a heterogeneous catalytic reaction, namely, a selective oxidization reaction of 4-methyl-3-decen-5-ol with an oxygen-containing gas using a metal catalyst that contains a catalytic metal deposited on a nanoparticle support.

Examples for the oxygen-containing gas include air, pure oxygen gas, air enriched with oxygen, pure oxygen diluted in an inert gas such as nitrogen, helium or argon.

A metal catalyst as used herein refers to a catalyst containing a catalytic metal, a nanoparticle support, and, optionally, a promoter metal, wherein the catalytic metal is deposited on the nanoparticle support.

The catalytic metal contained in the metal catalyst is typically a hydrogenation metal, a metal that catalyzes a hydrogenation or oxidation reaction. It can be selected from the group consisting of noble and transition metals, such as gold (Au), platinum (Pt), palladium (Pd), ruthenium (Ru), rhodium (Rh), iridium (Ir), iron (Fe), nickel (Ni), and manganese (Mn), or combinations thereof. The weight percentage of the catalytic metal, by weight of the metal catalyst, is in the range of 0.05 to 20%, preferably 0.1 to 20%, and more preferably 0.5 to 10%.

A promoter metal contained in the metal catalyst does not itself catalyze a hydrogenation or oxidation reaction. However, when combining with a catalytic metal, it will increase the catalytic effect (e.g., increasing reaction speed, selectivity, and/or yield) of the catalytic metal. Examples of a promoter metal are alkaline or alkaline-earth metals such as Li, Na, K, Rb Cs, Be, Mg, Ca, Sr, Ba, and combinations thereof.

The amount of the promoter metal is preferably between 1 and 40,000 ppm (e.g., 10 and 50,000 ppm, 10 and 20,000 ppm, 100 and 20000 ppm, 100 and 10,000 ppm, 200 and 5000 ppm, 400 and 4000 ppm) by weight of the metal catalyst.

The nanoparticle support is a nanoparticle of a metal oxide selected from the group consisting of oxides of alkaline-earths, transition metals, lanthanides and p-bloc elements, such as silicon dioxide ($SiO_2$), magnesium oxide (MgO), aluminum oxide ($Al_2O_3$), titanium dioxide ($TiO_2$), cerium dioxide ($CeO_2$), zirconium dioxide ($ZrO_2$), or mixtures thereof. Charcoal sometimes can also be used as a nanoparticle support in this invention.

In one embodiment, the metal catalyst is a gold catalyst containing gold deposited on a nanoparticle support (e.g., a cerium dioxide nanoparticle support). By weight of the gold catalyst, the gold content is 0.1 to 20% (e.g., 0.2 to 15% and 0.5 to 10%), and the cerium oxide nanoparticle support content is 80 to 99.9% (e.g., 85 to 99.8% and 90 to 99.5%).

In another embodiment, the metal catalyst is a sodium-doped gold catalyst containing gold and sodium deposited on a cerium dioxide nanoparticle support. The sodium content is 1 and 100,000 ppm (e.g., 1 and 40,000, 10 and 40,000 ppm, 100 and 20,000 ppm, 200 and 10,000 ppm, 400 and 5,000 ppm) by weight of the metal catalyst. By adding the promoter metal sodium to the gold catalyst, the selectivity and yield of the desired product is unexpectedly improved. Also improved is the selectivity towards the desired product (4-methyl-3-decen-5-one). Moreover, the presence of an alkaline metal increases the stability and reusability of the metal catalyst.

The metal catalyst may be prepared following known methods such as impregnation of a nanoparticle support with a catalytic metal salt aqueous solution obtained by dissolving a catalytic metal halogen acid or salt in water. As an illustration, a nanoparticle support (e.g., a $CeO_2$ nanoparticle) is immersed in a $HAuCl_4$ solution so that gold nanoparticles are absorbed onto the nanoparticle support. Another preparation method involves the precipitation of a catalytic metal (e.g., an insoluble metal hydroxide) onto a nanoparticle support.

The metal catalyst, before its use in reaction, can be further treated such as calcination (thermal treatment) at a temperature of 25 to 800° C. (e.g., 50 to 600° C., 50 to 400° C., 50 to 250° C., and 50 to 220° C.) in the presence of an oxidant or reduction gas (e.g., air and hydrogen gas), or an inert gas (nitrogen), in static or flow conditions.

Another post-synthesis treatment of the metal catalyst is the reduction of a catalytic metal compound in a solution of a primary or secondary alcohol such as phenylethanol at a pre-determined temperature (e.g., between 40 and 240° C.) under nitrogen flow for a period of 5 minutes to 24 hours. As an illustration, alcohol phenylethanol, under nitrogen flow, is added to a gold catalyst supported on cerium dioxide nanoparticle ($Au/CeO_2$). The weight ratio between $Au/CeO_2$ and phenylethanol is 1:100 to 1:2. The resultant suspension is then heated to a pre-determined temperature (e.g., 40 to 120° C.) for a period of 10 minutes to 5 hours (e.g., 15 minutes to 3 hours). Subsequently, the suspension is filtered and the reduced metal catalyst was washed several times (e.g., 1-10 times and 2-5 times) with an organic protic solvent such as acetone, ethanol, methanol, and isopropanol. The reduced metal catalyst (e.g., reduced $Au/CeO_2$) is then dried for several hours (e.g., 1 to 10 hours and 1 to 5 hours) at a temperature 50 to 100° C.

The combination of these post-synthesis treatments can be performed. Moreover, the metal catalyst can be used as prepared without any post-synthesis treatment.

The oxidation of 4-methyl-3-decen-5-ol is performed in the presence of one of the metal catalysts described above. The amount of the metal catalyst is typically in the range of 0.01 to 50% (e.g., 0.1 to 50%, 1 to 50%, 6 to 50%, 1 to 40%, 6 to 40%, 3 to 40%, 6.5 to 40%, 3 to 30%, 7 to 30%, 4 to 15%, and 7.5 to 20%) with respect to the weight of 4-methyl-3-decen-5-ol. By illustration, when oxidizing 1 gram of 4-methyl-3-decen-5-ol, it is preferred to use 0.03 to 0.4 grams (e.g., 0.06 to 0.4 grams) of the metal catalyst, namely, 3 to 40% (e.g., 6 to 40%) with respect to the weight of 4-methyl-3-decen-5-ol. In each of these metal catalysts, the catalytic metal is typically present at a level of 0.01 to 50% (e.g., 0.1 to 40%, 0.5 to 30% and 1 to 20%) by weight of the metal catalyst. The molar ratio of 4-methyl-3-decen-5-ol to the catalytic metal can be between 15:1 and 150000:1 (e.g., 20:1 to 20000:1, 20:1 to 1000:3, 50:1 to 5000:1, and 50:1 to 1000:3). In term of molar percent, the catalytic metal is present in an amount of 0.0007 to 6.7 molar % (e.g., 0.005 to 5 molar %, 0.3 to 5 molar %, 0.02 to 2 molar %, and 0.3 to 2 molar %) with respect to the mole of 4-methyl-3-decen-5-ol.

The oxidation of 4-methyl-3-decen-5-ol to 4-methyl-3-decen-5-one can be performed in a reactor filled with an oxygen-containing gas, either in a static condition (i.e., in a conventional static reactor) or in a flow of the oxygen-containing gas (i.e., in a flow reactor). In either condition, the oxygen-containing gas in the reactor preferably has a pressure of 0.1 to 30 bars, more preferably 1 to 15 bars (e.g., 2 to 10 bars and 3 to 6 bars). In a flow reactor, the oxygen-containing gas has a flow of 0.2 to 100 mL/min (preferably, 0.5 to 30 mL/min) for each gram of 4-methyl-3-decen-5-ol.

In some embodiments, the reaction temperature is in the range of 20 to 240° C. Preferably, it is in the range of 60 to 140° C. More preferably, it is in the range of 75 to 110° C.

The oxidization reaction can be performed in the presence of absence of a solvent. Exemplary solvents include nitriles (e.g., acetonitrile and benzonitrile), halogen- or non-halogen-containing alkyl and/or aromatic solvents (e.g., benzene, toluene and trifluorotoluene), carboxylic acid solvents (e.g., acetic and propionic acid).

In this invention, the oxidation reaction of 4-methyl-3-decen-5-ol produces water and the desired product 4-methyl-3-decen-5-one. When the oxidation reaction achieves its equilibrium, the ratios among 4-methyl-3-decen-5-ol, 4-methyl-3-decen-5-one, and water remains constant. To shift the equilibrium, water is removed from the reaction mixture using any distillation technique or, by adsorption using a drying agent such as a molecular sieve.

The oxidization reaction can be accelerated by a base. Optionally oxidizing 4-methyl-3-decen-5-ol is carried out in the presence of an inorganic base, an organic base, or a combination thereof. Preferably, the inorganic base is selected from the group consisting of alkaline and/or earth-alkaline hydroxides, carbonates, phosphates, and combinations thereof. The organic base can be selected from the group consisting of alkaline alcoholates, phosphazenes, amines, quaternary ammonium hydroxides, and combinations thereof.

The oxidation reaction occurs either in a batch reactor, a semicontinuous reactor, or a continuous reactor.

A batch reactor refers to a conventional static reactor, in which 4-methyl-3-decen-5-ol, the metal catalyst, and the oxygen-containing gas are secured in the reactor to allow the oxidization reaction to occur.

A semicontinuous or continuous reactor refers to a flow reactor including a single Continuous Stirred Tank Reactor (CSTR), multiple CSTRs in series, or a microreactor.

In some embodiments, liquid 4-methyl-3-decen-5-ol is pumped into a flow reactor together with the oxygen-containing gas. In other embodiments, 4-methyl-3-decen-5-ol is dissolved in a solvent or mixed in-line using a static mixer before entering the reactor. In still other embodiments, the reactor may include a catalyst retainer to prevent the metal catalyst from moving out of the reactor. In some embodiments, the reactor system is heated using a heating circulating oil bath or electrical heater. From the reactor system, the reaction mixture is collected in a product receiver. The reaction mixture is analyzed for reaction completion using an instrument such as Gas Chromatography (GC).

All parts, percentages and proportions referred to herein and in the claims are by weight unless otherwise indicated.

The values and dimensions disclosed herein are not to be understood as being strictly limited to the exact numerical values recited. Instead, unless otherwise specified, each such value is intended to mean both the recited value and a functionally equivalent range surrounding that value. For example, a value disclosed as "50%" is intended to mean "about 50%."

As used herein L is understood to be liter, mL is understood to be milliliter, M is understood to be mole/liter, m is understood to be meter, mm is understood to be millimeter, μm is understood to be micrometer, nm is understood to be nanometer, mol is understood to be moles, psig is understood to be pounds per square inch gauge, g is understood to be gram, kg is understood to be kilogram, and min is understood to be minutes.

The invention is described in greater detail by the following non-limiting examples. Without further elaboration, it is believed that one skilled in the art can, based on the description herein, utilize the present invention to its fullest extent.

All publications cited herein are incorporated by reference in their entirety.

Example 1

4-methyl-3-decen-5-one was prepared using metal catalyst Au/CeO$_2$ nanoparticle Synthesis of Catalyst I: Au/CeO$_2$ A cerium oxide (CeO$_2$) nanoparticle was prepared as a nanoparticle support for the metal catalyst. An aqueous solution of Ce(NO$_3$)$_4$ (375 mL, 0.8 M) was treated with an aqueous solution of ammonia (1.12 L, 0.8 M), under magnetic stirring at room temperature (i.e., 20° C.) to form a CeO$_2$ nanoparticle. Consequently, the dispersion of CeO$_2$ nanoparticle was heated to 100° C., in a closed PET vessel, for 24 hours. The resulting yellow precipitate was filtered and dried under vacuum overnight. The CeO$_2$ nanoparticle thus prepared showed a small particle size (diameter 10 nm) and a high surface area (180 m$^2$/g).

Gold nanoparticles were then deposited on the CeO$_2$ nanoparticles as follows. HAuCl4.3H2O (100 mg) was dissolved in water (100 mL) and the pH was adjusted to 10 to obtain a gold solution, which was then added to CeO$_2$ (1 g) nanoparticle suspension in water (50 mL). The pH of the resulting slurry was adjusted to 10. The slurry was stirred vigorously for 18 hours at room temperature to obtain Catalyst I, Au/CeO$_2$, as a solid precipitation, collected by filtration and washed with water.

Catalyst I was dried under vacuum at room temperature for 1 hour. The Au content was 4.5 wt % by weight of Catalyst I as determined by chemical analysis.

Synthesis of 4-methyl-3-decen-5-one using Catalyst I

In a three-necked-round flask equipped with a Dean Stark apparatus and a condenser, 1 g of 4-methyl-3-decen-5-ol was added to 75 mg of Catalyst I (the metal catalyst 7.5% by weight of 4-methyl-3-decen-5-ol and Au 0.34 mol % by mole of 4-methyl-3-decen-5-ol). A flow of air (10 mL/min) at atmospheric pressure was passed through the resultant mixture under stirring at a temperature of 100° C. The oxidization of 4-methyl-3-decen-5-ol was monitored by GC or GC-MS analysis of samples taken at different reaction times. In the GC analysis, dodecane was used as the external standard. After 7 hours, the product 4-methyl-3-decen-5-one was obtained at a yield of 76% with a selectivity of 96.5%.

The yield was calculated as follows: the actual amount of 4-methyl-3-decen-5-one obtained from the reaction (g)/the theoretical yield of 4-methyl-3-decen-5-one (g)×100%. The theoretical yield refers to the amount of 4-methyl-3-decen-5-one when all 4-methyl-3-decen-5-ol is converted without giving any by-product.

The selectivity refers to the molar percent of reacted 4-methyl-3-decen-5-ol that is converted to 4-methyl-3-decen-5-one.

Example 2

Synthesis of Catalyst II: Na (1000 ppm)-doped Au/CeO$_2$

Catalyst I was reduced using phenylethanol and doped with 1000 ppm sodium to obtain Catalyst II following the procedure below.

In a two-necked round flask equipped with a condenser, 12 mL of phenylethanol were added under a nitrogen flow (5 ml/min) followed by adding 1 g of Catalyst I (Au/CeO$_2$). The resultant mixture containing the solid catalyst was heated to 80° C. and held at this temperature for 2 hours under agitation. Subsequently, the solid catalyst was collected by filtration, washed exhaustively with acetone (500 mL), and dried for 3 hours at 100° C. Then the solid catalyst was suspended in 0.5 mL of an aqueous solution of sodium acetate (0.52 M).

Drying the suspension at 100° C. yielded Catalyst II, i.e., Na (1000 ppm)-doped Au/CeO$_2$.

Synthesis of 4-methyl-3-decen-5-one using Catalyst II

4-Methyl-3-decen-5-one was prepared following the same procedure as described in Example 1 except that Catalyst II was used instead of Catalyst I. The yield and selectivity of 4-methyl-3-decen-5-one were 83.5 and 98.5%, respectively.

Table 1 below summarizes the results obtained in Examples 1 and 2.

TABLE 1

| EXAMPLE | Catalyst | 4-methyl-3-decen-5-ol Conversion (%) | 4-methyl-3-decen-5-one yield (%) | 4-methyl-3-decen-5-one selectivity (%) |
|---|---|---|---|---|
| 1 | Au/CeO$_2$ | 79 | 76 | 96.5 |
| 2 | Na(1000 ppm)-Au/CeO$_2$ | 85 | 83.5 | 98.5 |

Example 3

Reuse of Catalyst II, Na (1000 ppm)-doped Au/CeO$_2$

Catalyst II used in the reaction described in Example 2 was collected and reused to prepare 4-methyl-3-decen-5-one following the same procedure in Example 2 above. After 7 hours of reaction time, the 4-methyl-3-decen-5-one yield and selectivity were 88 and 96.5, respectively.

Example 4

Synthesis of Catalyst IV: Au/HPA

Catalyst IV, i.e., gold supported on hydroxyapatite nanoparticle (Au/HPA), was prepared following the procedure as follows. Two solution were prepared: a first solution of Ca(NO$_3$)$_2$.4H$_2$O (15.74 g, 0.066 mol) in water (150 mL) and a second solution of (NH$_4$)$_2$HPO$_4$ (5.28 g, 0.04 mol) in water (120 mL). The pH of both solution was brought to pH=11 with concentrated ammonia solution (NH$_4$OH). To the first solution under agitation was added the second solution dropwise over a period of 30 minutes to produce a milky mixture, which was then stirred at 90° C. 2 hours. A HPA nanoparticle was formed, collected by filtration, washed with water, and dried at 120° C. for 16 hours.

Au nanoparticles were then deposited onto the HPA nanoparticle thus prepared. More specifically, a solution of urea (600 mg in 30 mL of water) was added to 1 g of HPA nanoparticle, followed by the addition of a HAuCl$_4$.3H$_2$O solution (35 mg in 5 mL of water). The resultant mixture was vigorously stirred at 90° C. for 4 hours to obtain an Au/HPA solid, which was collected by filtration, washed with water and acetone and dried by air. The Au/HPA solid was then reduced by NaBH$_4$ (0.07M, 15 mL in water) at room temperature for 30 minutes to obtain Catalyst IV.

Filtration, water washing, and drying at 100° C. overnight gave about 1 g of Catalyst IV: Au/HPA. The Au content was found to be 2 wt % as determined by chemical analysis.

Synthesis of 4-methyl-3-decen-5-one using Catalyst IV

In an autoclave, 1.48 g of 4-methyl-3-decen-5-ol were added to 250 mg of Catalyst IV (17% the metal catalyst by weight of 4-methyl-3-decen-5-ol and 0.34 mol % Au by mole of 4-methyl-3-decen-5-ol). A flow of air (20 mL/min) at atmospheric pressure was passed through the resultant mixture under stirring at a temperature of 100° C. The oxidization of 4-methyl-3-decen-5-ol was monitored by GC or GC-MS analysis.

After 4.5 hours, 4-methyl-3-decen-5-one was obtained with the yield and selectivity at 89 and 92%, respectively.

Example 5

Synthesis of Catalyst V: Pt—Au/CeO$_2$

Catalyst V, i.e., Au/CeO$_2$ doped with 200 ppm of platinum, was prepared as follows. A solution of 12.7 mg of chloroplatinic acid hexahydrate in 10 mL of water was prepared. 0.5 mL of this solution was then added to 1 g of Catalyst I described in Example 1. The resultant slurry was dried for 12 hours at 100° C. to obtain a Pt—Au/CeO$_2$ solid. Subsequently, the solid was added to 12 mL of phenylethanol under nitrogen flow (5 ml/min), heated to 80° C., and maintained at this temperature for 2 hours to obtain Catalyst V, which was collected by filtration, washed with acetone, and dried at 100° C. for 3 hours.

Synthesis of 4-methyl-3-decen-5-one using Catalyst V

In an autoclave, 1 g of 4-methyl-3-decen-5-ol was added to 75 mg of Catalyst V (the metal catalyst 7.5% by weight of 4-methyl-3-decen-5-ol and Au 0.34 mol % by mole of 4-methyl-3-decen-5-ol). A flow of air (10 mL/min) under a pressure of 4.5 bars was passed through the resultant mixture under stirring at a temperature of 100° C. The oxidization of 4-methyl-3-decen-5-ol was monitored by GC. After 1 hour, 4-methyl-3-decen-5-one was obtained at a yield of 53% and a selectivity of 88%.

Example 6

Synthesis of Catalyst VI: Mn—Au/CeO$_2$

Catalyst VI, i.e., Au/CeO$_2$ doped with 200 ppm of manganese, was prepared following the below procedure. A MnCl$_2$ solution was prepared by dissolving 18 mg of manganese (II) chloride tetrahydrate in 100 mL of water. 5 mL of this solution was added to 1 g of Catalyst I described above. The resultant suspension was stirred for 2 hours at room temperature. The Mn—Au/CeO$_2$ solid in the suspension was filtered and dried at 100° C. for 12 hours.

Consequently, the dried Mn—Au/CeO$_2$ was reduced using 12 mL of phenylethanol at 80° C. for 2 hours to obtain Catalyst V, which was collected by filtration, washed with acetone, and dried for 3 hours at 100° C.

Synthesis of 4-methyl-3-decen-5-one using Catalyst VI

4-Methyl-3-decen-5-one was prepared following the same procedure as described in Example 5 except that (i) Catalyst VI was used instead of Catalyst V and (ii) the reaction time was 3 hours instead of 1 hour. Its yield and selectivity were 68% and 88%, respectively.

Example 7

Synthesis of Catalyst VII: Fe—Au/CeO$_2$

Catalyst VII, i.e., Au/CeO$_2$ doped with 200 ppm of iron, was prepared as follows. A FeCl$_2$ solution was prepared by dissolving 12.5 mg of iron (II) acetate in 100 mL of water. 5 mL of this solution was added to 1 g of Catalyst I. The resultant suspension was stirred for 2 hours at room temperature. The Fe—Au/CeO$_2$ solid in the suspension was filtered and dried at 100° C. for 12 hours.

Consequently, the dried Fe—Au/CeO$_2$ was reduced using 12 mL of phenylethanol at 80° C. for 2 hours to obtain Catalyst VII, which was collected by filtration, washed with acetone, and dried for 3 hours at 100° C.

Synthesis of 4-methyl-3-decen-5-one using Catalyst VII

4-Methyl-3-decen-5-one was prepared following the same procedure as described in Example 5 except that Catalyst VII was used instead of Catalyst V. Its yield and selectivity were 52% and 88%, respectively.

Example 8

Synthesis of Catalyst VIII: Au/C

Catalyst VIII, i.e., gold (2 wt %) supported on a carbon nanoparticle, was prepared following the below procedure.

A first solution, i.e., Solution A, was prepared by dissolving 75 mg of HAuCl$_4$.3H$_2$O in 500 mL water.

A second solution, i.e., Solution B, was prepared by dissolving 75 mg of poly(vinyl alcohol) in 3.75 mL of water.

The two solutions were combined, followed by addition of a NaBH$_4$ (72.5 mg of NaBH$_4$ in 19 mL of water) dropwise. The pH of the resultant mixture was adjusted to 2 to obtain a reduced gold solution. Subsequently, 250 mL of this reduced gold solution was added to 0.626 g of carbon nanoparticle and stirred for 2 hours at room temperature to obtain Catalyst VIII, which was collected by filtration, washed with water, and dried at 60° C. overnight. Catalyst VIII, i.e., Au/C, contained 2 wt % gold.

Synthesis of 4-methyl-3-decen-5-one using Catalyst VIII: Au/C

4-Methyl-3-decen-5-one was prepared following the same procedure as described in Example 5 except that (i) 150 mg of Catalyst VIII was used instead of 75 mg of Catalyst V, and (ii) the reaction time was 5 hours instead of 1 hour. Its yield and selectivity were 49% and 57%, respectively.

Examples 9-13

Example 9: Synthesis of 4-methyl-3-decen-5-one using 2 wt % Catalyst II

In an autoclave, 1 g of 4-methyl-3-decen-5-ol was added to 20 mg of Catalyst II (Au/CeO$_2$ 2% by weight of 4-methyl-3-decen-5-ol and Au 0.09 mol % by mole of 4-methyl-3-decen-5-ol). A flow of oxygen (10 mL/min) under pressure at 4.5 bars was passed through the resultant mixture under stirring at a temperature of 100° C. The oxidization of 4-methyl-3-decen-5-ol was monitored by GC. Samples were drawn at different reaction time points and analyzed for the yield and selectivity of 4-methyl-3-decen-5-one. The results were shown in FIG. 1 and Table 2 below.

Example 10: Synthesis of 4-methyl-3-decen-5-one using 5 wt % Catalyst II

Another reaction was carried out using 5 wt % Catalyst II (0.23 mol % Au) by weight of 4-methyl-3-decen-5-ol following the same procedure above except that different amount of the metal catalyst was used. The results were shown in FIG. 1 and Table 2 below.

Example 11: Synthesis of 4-methyl-3-decen-5-one using 7.5 wt % Catalyst II

A third reaction was carried out using 7.5 wt % Catalyst II (0.34 mol % Au) by weight of 4-methyl-3-decen-5-ol following the same procedure above except that different amount of the metal catalyst was used. The results were shown in FIG. 1 and Table 2 below.

Example 12: Synthesis of 4-methyl-3-decen-5-one using 10 wt % Catalyst II

A fourth reaction was carried out using 10 wt % Catalyst II (0.46 mol % Au) by weight of 4-methyl-3-decen-5-ol following the same procedure above except that different amount of the metal catalyst was used. The results were shown in FIG. 1 and Table 2 below.

Example 13: Synthesis of 4-methyl-3-decen-5-one using 20 wt % Catalyst II

A fifth reaction was carried out using 20 wt % Catalyst II (0.92 mol % Au) by weight of 4-methyl-3-decen-5-ol following the same procedure above except that different amount of the metal catalyst was used. The results were shown in FIG. 1 and Table 2 below.

TABLE 2

| Catalyst wt % | Au mol % | Time (hours) | Veridian Yield % | Veridian Selectivity % |
|---|---|---|---|---|
| 2 | 0.09 | 12.5 | 38 | 93 |
| 5 | 0.23 | 9 | 53 | 92 |
| 7.5 | 0.34 | 9 | 92 | 95 |
| 10 | 0.46 | 2.7 | 95 | 97 |
| 20 | 0.92 | 1 | 93 | 96 |

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

Indeed, to achieve the purpose of preparing 4-methyl-3-decen-5-one with a high yield and selectivity, one skilled in the art can choose different catalytic metals, nanoparticle supports, doping metals, reaction temperature, oxygen sources, pressure, and/or reaction time. Further, the ratios among 4-methyl-3-decen-5-ol, metal catalyst, catalytic metal, and doping metal can also be determined by a skilled artisan through assays known in the art.

From the above description, a skilled artisan can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A method of preparing 4-methyl-3-decen-5-one, the method comprising oxidizing 4-methyl-3-decen-5-ol in the presence of (i) an oxygen-containing gas and (ii) a metal catalyst, wherein the metal catalyst is a sodium-doped gold catalyst containing gold (Au) and sodium (Na) deposited on a nanoparticle support.

2. The method of claim 1, wherein the nanoparticle support is iron oxide, titanium oxide, cerium oxide, zirconium oxide, alumina, charcoal, hydroxyapatite, or any combination thereof.

3. The method of claim 2, wherein the nanoparticle support is cerium oxide.

4. The method of claim 3, wherein the metal catalyst is doped with Na in an amount of 10 to 40,000 ppm by weight of the metal catalyst.

5. The method of claim 1, wherein Au is present in an amount of 0.2 to 10% by weight of the metal catalyst.

6. The method of claim 1, wherein the oxygen-containing gas is provided in the form of an oxygen gas, air, stripped air, enriched air, or any combination thereof.

7. The method of claim 1, wherein the reaction is performed at a temperature of 20 to 240° C., and at a pressure of 0.1 to 20 bars.

8. The method of claim 1, wherein the reaction is performed in the presence or absence of a solvent, when a solvent is used, the solvent is selected from the group consisting of a nitrile, a halogen- or non-halogen-containing alkyl and/or aromatic solvent, a carboxylic acid solvent, and any combination thereof.

9. The method of claim 1, wherein the reaction is performed in a batch reactor or a continuous reactor.

10. The method of claim 9, wherein the continuous reactor is a single CSTR, multiple CSTRs in series, or a microreactor.

11. The method of claim 9, wherein the continuous reactor is a packed bed reactor packed with a glass bead, metal catalyst, or a combination thereof.

12. The process of claim 11, wherein the catalyst has a volume in the reactor ranging from 20 to 90%.

13. The process of claim 10, wherein the continuous reactor is a microreactor containing channels each having an internal diameter ranging from 0.1 to 200 mm.

14. The process of claim 4, wherein the metal catalyst is doped with Na in an amount of 100 to 20,000 ppm by weight of the metal catalyst.

15. The process of claim 14, wherein the oxygen-containing gas is provided in the form of an oxygen gas, and the reaction is performed in the absence of a solvent at a temperature of 60 to 140° C. and a pressure of 1 to 15 bars.

16. The process of claim 1, wherein the catalyst is present in the amount of 6 to 50% by weight of 4-methyl-3-decen-5-ol.

17. The process of claim 16, wherein the metal catalyst is a sodium-doped gold catalyst containing gold and sodium deposited on a cerium dioxide nanoparticle support.

18. The process of claim 17, wherein the sodium content is between 200 and 10,000 ppm by weight of the metal catalyst.

19. The method of claim 18, wherein the oxygen-containing gas is provided in the form of an oxygen gas, air, stripped air, enriched air, or any combination thereof.

20. The method of claim 19, wherein the reaction is performed at a temperature of 20 to 240° C., and at a pressure of 0.1 to 20 bars.

* * * * *